US008756081B2

(12) United States Patent
Hirose et al.

(10) Patent No.: US 8,756,081 B2
(45) Date of Patent: Jun. 17, 2014

(54) MEDICAL INFORMATION MANAGEMENT SYSTEM AND MANAGEMENT APPARATUS

(71) Applicant: Olympus Medical Systems Corp., Tokyo (JP)

(72) Inventors: Koichi Hirose, Tokyo (JP); Hirofumi Inaba, Tokyo (JP); Koji Suzuki, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/858,982

(22) Filed: Apr. 9, 2013

(65) Prior Publication Data

US 2013/0297343 A1 Nov. 7, 2013

Related U.S. Application Data

(63) Continuation of application No. PCT/JP2012/006294, filed on Oct. 2, 2012.

(30) Foreign Application Priority Data

Oct. 11, 2011 (JP) .................................. 2011-224301

(51) Int. Cl.
*G06Q 10/00* (2012.01)
*G06Q 50/00* (2012.01)
*A61B 5/00* (2006.01)
*G06F 19/00* (2011.01)

(52) U.S. Cl.
USPC ................................................. 705/3; 705/2

(58) Field of Classification Search
USPC .......................................................... 705/2–3
See application file for complete search history.

(56) References Cited

U.S. PATENT DOCUMENTS

| 6,551,243 | B2 * | 4/2003 | Bocionek et al. ............. 600/300 |
| 2002/0099571 | A1 * | 7/2002 | Waku et al. ....................... 705/2 |

(Continued)

FOREIGN PATENT DOCUMENTS

| JP | 8-263570 A | 10/1996 |
| JP | 2001-46326 A | 2/2001 |

(Continued)

OTHER PUBLICATIONS

English language abstract only of Japanese Patent Application Publication No. 2006-087669 dated Apr. 6, 2006.

(Continued)

*Primary Examiner* — Joy Chng
(74) *Attorney, Agent, or Firm* — Scully, Scott, Murphy & Presser, P.C.

(57) ABSTRACT

In a monitor device, an input unit inputs patient identification information, an information acquiring unit acquires state information on a state of a patient, and a transmission unit transmits the patient identification information and the state information to a management apparatus. In the management apparatus, biological information acquiring unit acquires the patient identification information, the state information, and identification information on the monitor device. A determination unit determines, when the acquired patient identification information and that stored in a storage device match each other, whether the acquired device identification information and the device identification information mapped to the location information stored in the storage device are the same as each other. When they are the same as each other, a storage management unit stores the acquired state information by associating it with the patient identification information stored in the storage device.

5 Claims, 4 Drawing Sheets

(56) References Cited

U.S. PATENT DOCUMENTS

| | | | |
|---|---|---|---|
| 2005/0055242 A1* | 3/2005 | Bello et al. | 705/2 |
| 2007/0185736 A1* | 8/2007 | Cervi et al. | 705/2 |
| 2011/0066260 A1* | 3/2011 | Condurso et al. | 700/83 |
| 2012/0029313 A1* | 2/2012 | Burdett et al. | 600/301 |

FOREIGN PATENT DOCUMENTS

| | | |
|---|---|---|
| JP | 2002-312472 A | 10/2002 |
| JP | 2006-221617 A | 8/2006 |
| JP | 2006-244410 A | 9/2006 |
| JP | 4473690 B2 | 3/2010 |
| JP | 2011-181084 A | 9/2011 |
| JP | 2011-186802 A | 9/2011 |
| WO | 2010/047081 A1 | 4/2010 |
| WO | 2010/119822 A1 | 10/2010 |

OTHER PUBLICATIONS

International Search Report PCT/JP2012/006294 dated Dec. 18, 2012, together with an English language translation.

* cited by examiner

MEDICAL INFORMATION MANAGEMENT SYSTEM AND MANAGEMENT APPARATUS

CROSS-REFERENCE TO RELATED APPLICATIONS

This application is based upon and claims the benefit of priority from the prior Japanese Patent Application No. 2011-224301, filed on Oct. 11, 2011, the entire contents of which are incorporated herein by reference.

BACKGROUND OF THE INVENTION

1. Field of the Invention

The present invention relates to an information management technique, and in particular, to a medical information management technique for managing information on medical practice.

2. Description of the Related Art

In a medical site, when a doctor performs an examination, a treatment, or the like, vital sign monitor (VSM) for monitoring biological information on a patient is used. The VSM is a device for measuring an arterial oxygen saturation ($SpO_2$) and a pulse rate of a patient to display them in real time. Some of the VSMs display an electrocardiogram, blood pressure, and body temperature, etc. A doctor performs an examination or a treatment while checking biological information on a patient with the VSM.

Japanese Patent Application Publication No. 1996-263570 discloses a system in which a first medical diagnostic imaging device and a second medical diagnostic imaging device are connected with each other via a communication line. In this system, the first medical diagnostic imaging device transmits data for setting imaging conditions to the second medical diagnostic imaging device through this communication line, and the second medical diagnostic imaging device uses the imaging conditions by extracting them from the received data for setting imaging conditions. Japanese Patent Publication No 4473690 discloses an image inspection device. In the image inspection device, when the patient identification information on medical image data collected in the past and that of medical image data newly collected match each other; and when the respective patient information added to both the medical image data are different from each other, the patient information added to the medical image data collected in the past can be replaced by that added to the medical image data newly collected.

It is preferable that biological information measured with the VSM is stored by being associated with execution information on an examination, a treatment, or the like. In some countries, it is obligated to store biological information and execution information by associating them with each other. Because each of biological information and execution information is generated by being connected to patient identification information (patient ID) for identifying a patient, it can be considered that the processing for associating the biological information and the execution information with each other (hereinafter, referred to as "association processing"), performed when the respective patient ID match each other, has basically no problem.

However, it can occur that, for example, patient ID is erroneously inputted to the VSM and the erroneously inputted patient ID, to which biological information is connected, accidentally matches another patient ID. Accordingly, it is not preferable that association processing is performed when both patient ID only match each other, because the biological information connected to erroneously inputted patient ID may be associated with the execution information on another patient. In addition, when a patient undergoes a plurality of examinations or treatments, a plurality of pieces of execution information are sometimes generated for the person. In such a case, the biological information should be associated with one of the execution information; however, it is difficult to perform association processing when both patient ID match each other, because the patient ID, to which the biological information is connected, matches the patient ID, to which the plurality of pieces of execution information are connected. Accordingly, there is a demand for a technique in which biological information and execution information are stored by being associated with each other easily and surely.

SUMMARY OF THE INVENTION

The present invention has been made in view of these situations, and a purpose of the invention is to provide a technique for efficiently associating a plurality of pieces of information with each other.

In order to solve the aforementioned problem, a medical information management system according to an aspect of the present invention comprises: a management apparatus operative to manage information on medical practice for a patient; and a device able to communicate with the management apparatus via a network. The device includes: an input unit operative to input patient identification information; a first acquiring unit operative to acquire state information on a state of a patient; and a transmission unit operative to transmit the patient identification information and the state information. The management apparatus includes: a second acquiring unit operative to acquire the patient identification information, the state information, and identification information on a device; a holding unit operative to hold both location information for specifying a location where medical practice is executed and identification information on a device installed in the location, by mapping them to each other; a storage unit operative to store execution information on medical practice for a patient by mapping it to patient identification information and location information for specifying a location where medical practice has been executed; a determination unit operative to determine, when the patient identification information acquired by the second acquiring unit matches the patient identification information stored in the storage unit, whether the device identification information acquired by the second acquiring unit is the same as the device identification information mapped to the location information stored in the storage unit; and a storage management unit operative to store, when it is determined that both the device identification information are the same as each other, the state information acquired by the second acquiring unit in the storage unit by associating it with the patient identification information.

Another aspect of the present invention is a management apparatus operative to store execution information on medical practice for a patient by associating it with state information on a patient acquired by medical equipment. The management apparatus comprises: an acquiring unit operative to acquire patient identification information and state information, which are acquired by medical equipment, and identification information on the medical equipment; a holding unit operative to hold both location information for specifying a location where medical practice is executed and identification information on medical equipment installed in the location, by mapping them to each other; a storage unit operative to store execution information on medical practice for a patient by mapping it to patient identification information and location information for specifying a location where medical practice has been executed; a determination unit operative to determine, when the patient identification information acquired by the acquiring unit matches the patient identification information stored in the storage unit, whether the device identification information acquired by the acquiring unit is the same as the device identification information mapped to the location information stored in the storage unit; and a storage management unit operative to store, when it is determined that both the device identification information are the same as each other, the state information acquired by the acquiring unit in the storage unit by associating it with the patient identification information.

Optional combinations of the aforementioned constituting elements, and implementations of the invention in the form of methods, apparatuses, systems, or the like may also be practiced as additional modes of the present invention.

BRIEF DESCRIPTION OF THE DRAWINGS

Embodiments will now be described, byway of example only, with reference to the accompanying drawings which are meant to be exemplary, not limiting, and wherein like elements are numbered alike in several Figures, in which.

DETAILED DESCRIPTION OF THE INVENTION

The invention will now be described by reference to the preferred embodiments. This does not intend to limit the scope of the present invention, but to exemplify the invention.

Figure 1:
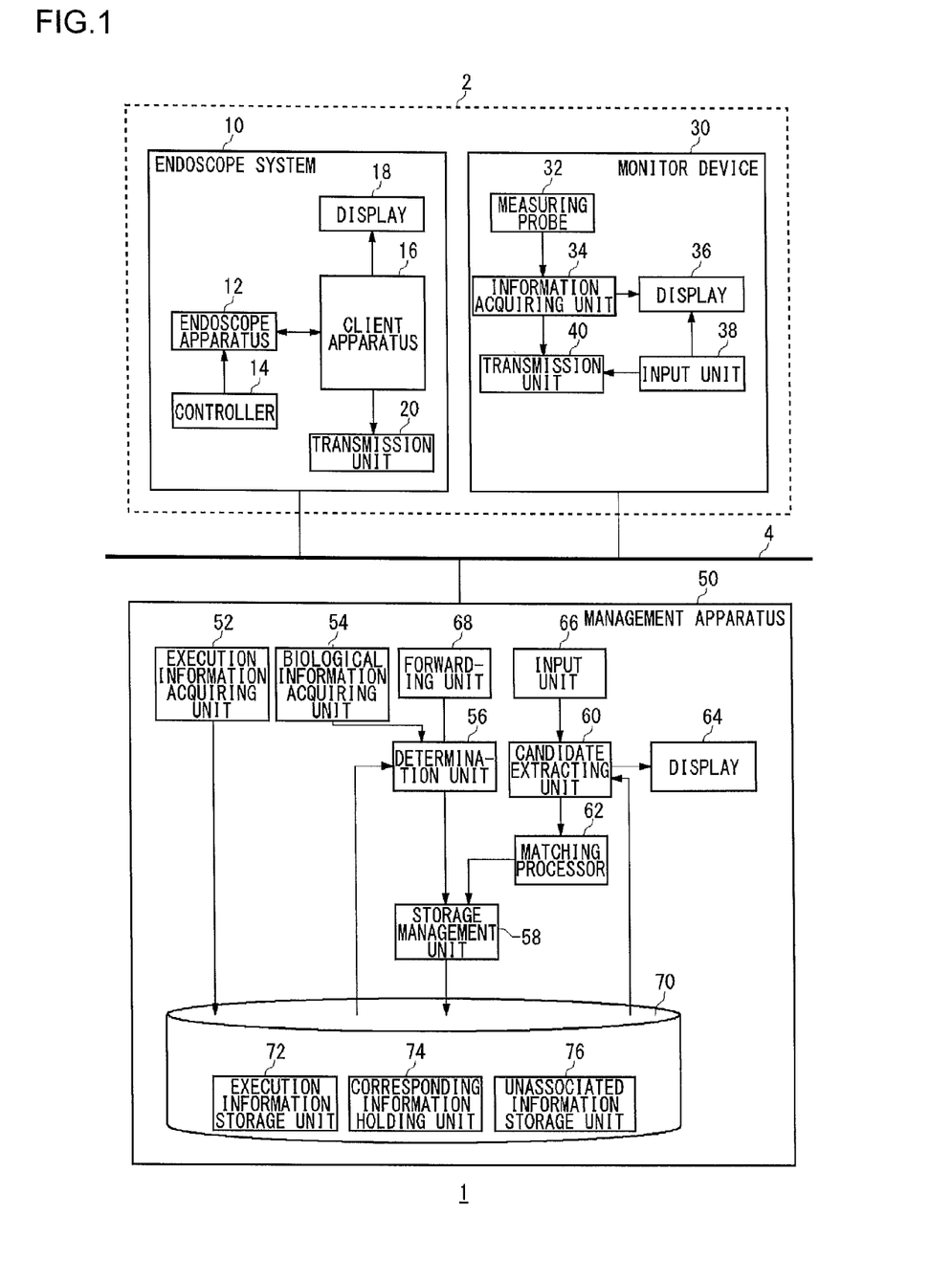
FIG. 1 is a view illustrating a structure of a medical information management system according to an embodiment of the present invention.

FIG. 1 is a view illustrating a structure of a medical information management system 1 according to an embodiment of the present invention. The medical information management system 1 of the embodiment is used for managing information on endoscopic examinations performed in medical facilities, such as a hospital. The medical information management system 1 comprises an endoscope system 10, a monitor device 30, and a management apparatus 50. The endoscope system 10, the monitor device 30, and the management apparatus 50 are communicably connected with each other via TCP/IP protocol over a network 4, such as an intranet, a local area network (LAN), or the like.

The management apparatus 50 manages the information on medical practice for a patient. Specifically, the management apparatus 50 performs processing for associating a plurality of pieces of information for a patient with each other (hereinafter, the processing is referred to as "association processing"). In an embodiment illustrated in FIG. 1, the management apparatus 50 stores, in a storage device 70, the information transmitted from each of the endoscope system 10 and the monitor device 30 by associating them with each other. In addition to the execution information on an endoscopic examination, the management apparatus 50 can also associate the execution information on an examination of another type, a treatment, or an operation, with the information on medical practice for the same patient. Hereinafter, an embodiment will be described, in which, when a doctor is performing an endoscopic examination for a patient by is using the endoscope system 10 while checking biological information (vital sign) of the patient with the monitor device 30, the management apparatus 50 performs processing for associating the execution information transmitted from the endoscope system 10 with the biological information transmitted from the monitor device 30.

The monitor device 30 includes a measuring probe 32, an information acquiring unit 34, a display 36, an input unit 38, and a transmission unit 40. The monitor device 30 is used for monitoring biological information on a patient and is referred to as a vital sign monitor. The monitor device 30, in which a pulse oximeter is incorporated to measure an arterial oxygen saturation ($SpO_2$) and a pulse rate, etc., of a patient, displays them in real time. Before starting a measurement with the monitor device 30, medical staff, such as a doctor, a nurse, or the like, inputs patient identification information for identifying a patient by using the input unit 38. The input unit 38 is a keyboard or a touch panel, and medical staff inputs patient identification information by operating the input unit 38. Alternatively, the input unit 38 may be an optical or magnetic reading means. When patient identification information is readably written in the wristband of a patient, etc., the patient identification information may be inputted to the monitor device 30 by being read with the input unit 38.

Specifically, the patient identification information to be inputted includes the name and the ID number of a patient. Of the name and the ID number of a patient, at least the ID number is information for uniquely specifying a patient in a hospital facility, and hence it is preferable that the ID number is inputted as patient identification information. Hereinafter, the patient identification information is sometimes referred to as "patient ID"; however, the patient ID is not limited to the name and the ID number of a patient, but may be information with which a patient can be uniquely specified, and may be, for example, information in which the name of a patient and the ID number thereof are combined together.

The measuring probe 32 includes a sensor and is attached to a fingertip of a patient. The information acquiring unit 34 periodically receives sensor information detected by the sensor in the measuring probe 32. The information acquiring unit 34 converts the detected sensor information into display information, and acquires state information on a state of a patient. Herein, the state information means biological information, such as a pulse rate, an arterial oxygen saturation, or the like. The display 36 displays the biological information acquired by the information acquiring unit 34 in real time, and a nurse or a doctor monitors the biological information displayed on the display 36.

Figure 2:
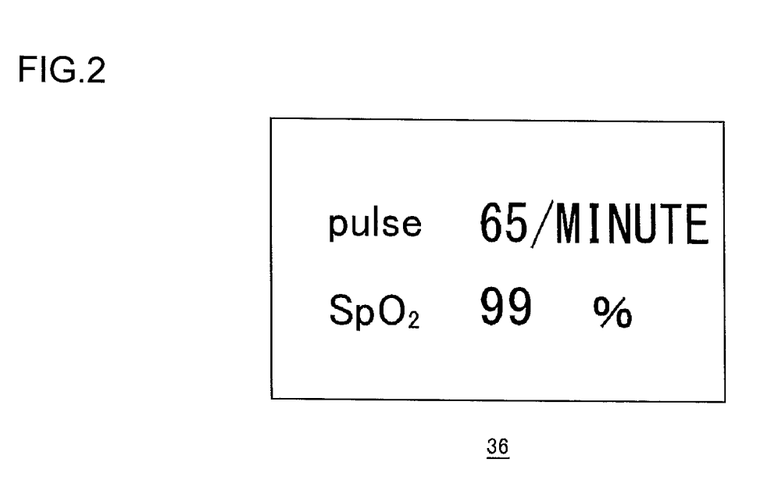
FIG. 2 is a view illustrating an example of biological information displayed on a display.

FIG. 2 illustrates an example of the biological information displayed on the display 36. In FIG. 2, a pulse rate (pulse) and an arterial oxygen saturation ($SpO_2$) are displayed as the biological information. Alternatively, biological information, such as an electrocardiogram, blood pressure, body temperature, or the like, may be displayed.

The endoscope system 10 includes an endoscope apparatus 12, a controller 14, a client apparatus 16, a display 18, and a transmission unit 20. An endoscopic examination is executed in accordance with an order for specifying patient identification information and an examination type, etc. The order specifies the content of medical practice including, in addition to an endoscopic examination, an examination of another type and an operation, and a doctor executes medical practice on the assumption that an order exists. The order is issued by a hospital information system (HIS) and managed by the management apparatus 50. Alternatively, the management apparatus 50 may acquire an order from the HIS. Alternatively, the management apparatus 50 may issue an order by taking charge of the function of issuing orders. Before the start of an endoscopic examination, patient identification information, such as the name and the ID number of a patient, and information, such as an examination type, the name of an examination room, a scheduled start time of the examination, and a scheduled end time thereof, which are included in an order, are displayed on the display 18 to be checked by a nurse or a doctor.

The endoscope apparatus 12 has an endoscope body (probe) to be inserted into the body cavity of a patient, so that an internal image is taken by a solid-state image sensing device, such as a CCD located at the tip of the probe, and an image signal is acquired. The controller 14 is formed by a switch, a keyboard, a pointing device, such as a mouse, a trackball, or the like, a touch panel, and a microphone, etc., and is used for generating an input instruction for the endoscope apparatus 12, such as start of an examination by a doctor, end thereof, a specified imaging condition, an instruction for capturing an image, or the like. The controller 14 may be formed integrally with the endoscope apparatus 12.

The endoscope apparatus 12 has a video processor for processing a signal captured by the endoscope probe. The video processor performs amplification, noise removal, analog-digital conversion, gain adjustment, adjustment of a luminance ratio, and filtering, etc., on the acquired image signal, so that a video signal, for displaying the image taken by the solid-state image sensing device on a monitor (not illustrated) as a live image, is generated. The monitor receives a video signal to display as a live image. While watching the live image, a doctor operates the controller 14 to generate an instruction for capturing an image. The endoscope apparatus 12 may record a captured image as an image file based on the instruction for capturing an image. Alternatively, a video signal may also be transmitted to the client apparatus 16, and the client apparatus 16 may record, upon receiving an instruction for capturing an image, the captured image at the time of reception as an image file. Upon receiving an instruction for ending the examination, the client apparatus 16 collects the captured image files to generate execution information on an endoscopic examination. The execution information on the medical practice for a patient includes a captured endoscope image file, which is collected as a piece of examination information along with patient identification information, examination start time, examination end time, location information (name of examination room), and order ID. After an examination is ended, the transmission unit 20 transmits the examination information to the management apparatus 50.

The functions of the client apparatus 16 may be achieved by, for example, a single computer, but may be achieved by a plurality of computers. As described later, the state information acquired by the information acquiring unit 34 in the monitor device 30 may be transmitted to the client apparatus 16 via the management apparatus 50 to be displayed on the display 18 in real time. A nurse can check the state of a patient by watching the biological information displayed on the display 18. For example, when the monitor device 30 does not include the display 36, it is effective to display biological information on the display 18 in real time.

The management apparatus 50 includes an execution information acquiring unit 52, a biological information acquiring unit 54, a determination unit 56, a storage management unit 58, a candidate extracting unit 60, a matching processor 62, a display 64, an input unit 66, a forwarding unit 68, and the storage device 70. The storage device 70 is formed by a hard disk drive, etc., and has an execution information storage unit 72, a corresponding information holding unit 74, and an unassociated information storage unit 76.

In an embodiment, the management apparatus 50 acquires the execution information on an endoscopic examination, which has been generated in the endoscope system 10, and the state information (biological information) of a patient, which has been generated in the monitor device 30, and performs processing for associating them with each other. This association processing is performed on the condition that, as a basic principle, the patient identification information in the execution information on an endoscopic examination and that in biological information on a patient match each other.

However, patient identification information is manually inputted in the monitor device 30 in most cases, and hence the possibility that the information may be erroneously inputted cannot be denied. Further, when one patient undergoes a plurality of examinations, a plurality of pieces of execution information on the examinations are generated. In this case, if association processing is performed only based on the matched patient identification information, there occurs a situation in which it is difficult to determine which execution information is to be associated with the biological information on the monitor device 30.

Accordingly, the management apparatus 50 is configured to perform processing for associating execution information with biological information based on the fact that a location where medical practice has been executed and a location where the monitor device 30 is arranged match each other. In the embodiment in FIG. 1, a situation is illustrated, in which the endoscope system 10 and the monitor device 30 are installed in the same examination room 2. The corresponding information holding unit 74 holds location information for specifying a location where medical practice is executed and identification information on a device installed in the location, by mapping them to each other. In this embodiment, the corresponding information holding unit 74 holds the location information for specifying the examination room 2 where an endoscopic examination is executed and the identification information (e.g., MAC address) of the monitor device 30 installed in the examination room 2, by mapping them to each other.

In the embodiment described below, the management apparatus 50 stores execution information and biological information in the storage device 70 by connecting them to an order. By storing them with being connected to an order, processing for associating the execution information with the biological information can be achieved. Alternatively, the management apparatus 50 may create, for example, a record for every order in the storage device 70 such that execution information and biological information are associated with each other by storing them in a predetermined field.

In the monitor device 30, the transmission unit 40 periodically transmits patient identification information and biological information to the management apparatus 50 via the network 4. The information acquiring unit 34 periodically provides the transmission unit 40 with the biological information, which is generated for displaying on the display 36, and the transmission unit 40 periodically transmits the biological information. The transmission unit 40 may transmit the biological information to the management apparatus 50 at intervals of, for example, 1 second. In the management apparatus 50, the biological information acquiring unit 54 acquires the patient identification information and the biological information transmitted via TCP/IP protocol from the transmission unit 40.

Upon acquiring the biological information, the biological information acquiring unit 54 acquires the device identification information on the monitor device 30 by using the IP address transmitted along with the biological information.

For example, the biological information acquiring unit 54 transmits a ping command for the acquired IP address, and after receiving a response, the biological information acquiring unit 54 acquires the device identification information (MAC address) of the monitor device 30 by transmitting an arp command. Alternatively, the biological information acquiring unit 54 may acquire device identification information via the IP address of the monitor device 30 when first acquiring the biological information, so that the device identification information is no more acquired thereafter.

The determination unit 56 determines whether the patient identification information acquired by the biological information acquiring unit 54 matches that stored in the execution information storage unit 72. The execution information storage unit 72 stores patient identification information and location information for specifying a location where an examination, etc., is executed, these information forming a record created for every order and being included in the order. The determination unit 56 determines whether the patient identification information acquired by the biological information acquiring unit 54 matches that stored in the execution information storage unit 72. This determination processing is performed with the determination unit 56 searching for a record including the patient identification information acquired by the biological information acquiring unit 54 in the execution information storage unit 72. Herein, when both the patient identification information does not match each other, that is, when a record including the patient identification information acquired by the biological information acquiring unit 54 does not exist in the execution information storage unit 72, the determination unit 56 determines that the biological information is not to be associated with the patient identification information stored in the execution information storage unit 72.

On the other hand, when both the patient identification information match each other, the determination unit 56 determines whether the device identification information acquired by the biological information acquiring unit 54 is the same as that mapped to the location information stored in the execution information storage unit 72. Specifically, when a record including the patient identification information acquired by the biological information acquiring unit 54 exists in the execution information storage unit 72, the determination unit 56 extracts location information from the record. In this embodiment, the extracted location information is one for specifying the examination room 2. The determination unit 56 reads out the device identification information mapped to the location information on the examination room 2 by referring to the content held by the corresponding information holding unit 74 to compare it with the device identification information acquired by the biological information acquiring unit 54. Herein, when both the device identification information are the same as each other, the determination unit 56 determines that the execution information in the endoscope system 10 and the biological information in the monitor device 30 are for the same patient, and that they have been acquired in the same examination room 2. When receiving a determination result by the determination unit 56, the storage management unit 58 stores the state information (biological information) acquired by biological information acquiring unit 54 by mapping it to the patient identification information stored in the execution information storage unit 72. Thereby, execution information and biological information can be appropriately associated with each other with a location being a key, even if a plurality of examinations or operations are executed for a single patient.

The biological information acquiring unit 54 acquires state information from the monitor device 30 at intervals of 1 second. The storage management unit 58 may store, at a predetermined sampling period, the state information acquired by the biological information acquiring unit 54 by associating it with the patient identification information stored in the execution information storage unit 72. For example, the storage management unit 58 may store the state information, acquired at intervals of 5 minutes, in the execution information storage unit 72.

The forwarding unit 68 forwards the state information, acquired by the biological information acquiring unit 54 at intervals of 1 second, to the endoscope system 10. Thereby, in the endoscope system 10, the client apparatus 16 can display the state formation on the display 18 in real time.

When an examination is ended in the endoscope system 10, the transmission unit 20 transmits the examination information on a patient to the management apparatus 50 via the network 4. As described above, the examination information includes patient identification information, execution information, examination start time, examination end time, location information (name of examination room), and order ID. In the management apparatus 50, when acquiring the examination information, the execution information acquiring unit 52 stores, in the record of the execution information storage unit 72, the patient identification information, the execution information, the examination start time, the examination end time, and the location information (name of examination room), by mapping them to each other based on order ID. Thereby, the management apparatus 50 can store execution information and biological information by appropriately associating them with each other.

On the other hand, when the determination unit 56 determines that the device identification information acquired by the biological information acquiring unit 54 is not the same as that mapped to the location information stored in the execution information storage unit 72, the storage management unit 58 stores, upon receiving the determination result, the biological information in the unassociated information storage unit 76 as unassociated information. Thereby, the unassociated information storage unit 76 stores biological information not associated with patient identification information.

Figure 3:
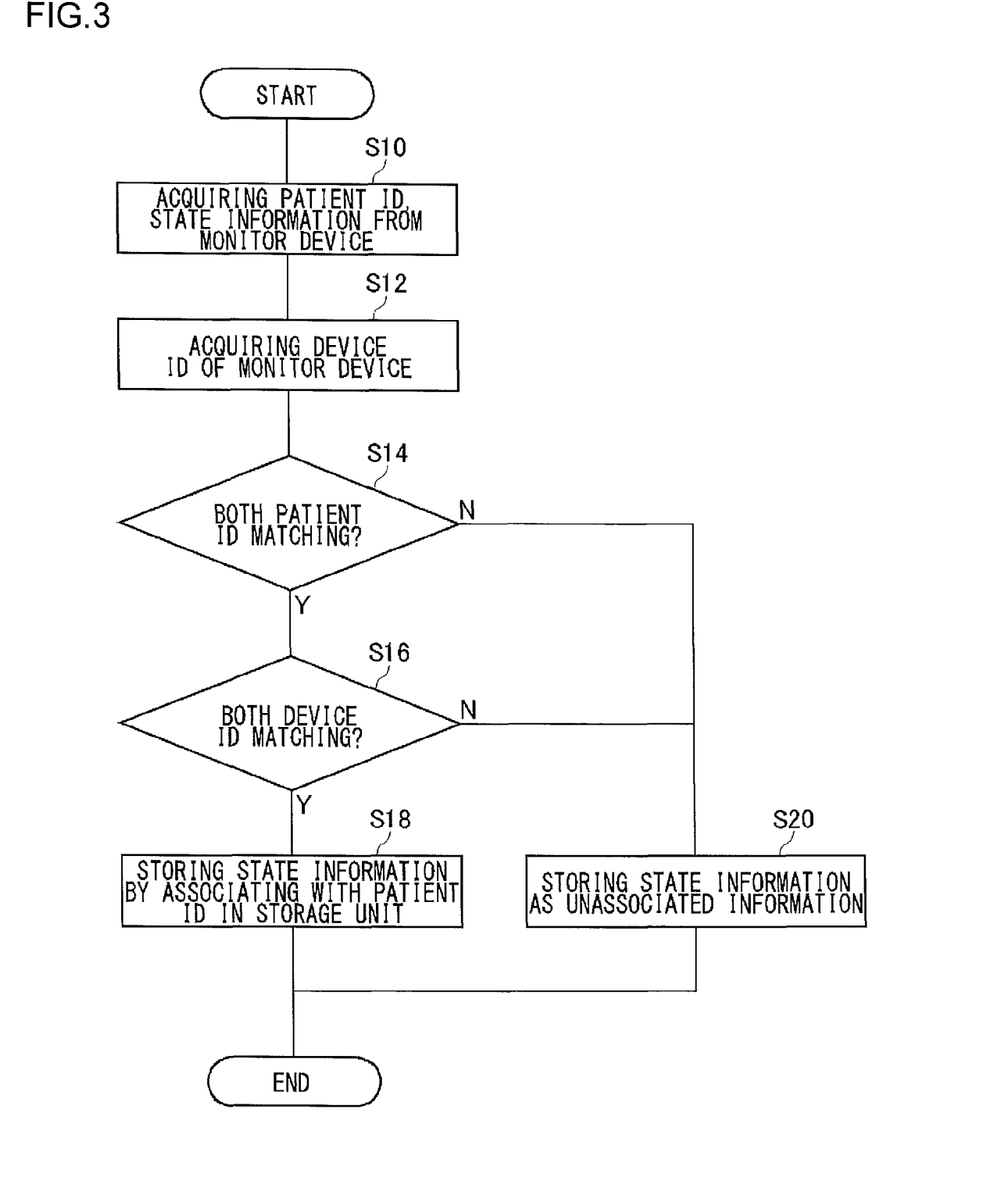
FIG. 3 is a view illustrating a flowchart of association processing by a management apparatus.

FIG. 3 illustrates a flowchart of association processing by the management apparatus 50. The biological information acquiring unit 54 acquires patient identification information (patient ID) and state information (biological information) from the monitor device 30 (S10). In addition, the biological information acquiring unit 54 acquires device ID (MAC address) from the IP address of the monitor device 30 (S12).

The determination unit 56 determines whether the patient ID acquired in S10 matches the patient ID stored in the execution information storage unit 72 (S14). When they do not match each other (S14/N), the storage management unit 58 stores the patient ID and the state information acquired in S10 in the unassociated information storage unit 76 as unassociated information (S20). On the other hand, when both the patient ID match each other (S14/Y), the determination unit 56 extracts the location information mapped to the patient ID in the execution information storage unit 72, and acquires the device ID mapped to the extracted location information by referring to the corresponding information holding unit 74. The determination unit 56 determines whether the device ID acquired in S12 matches that mapped to the location information (S16). When both the device ID do not match each other (S16/N), the storage management unit 58 stores the patient ID and the state information acquired in S10 in the unassociated information storage unit 76 as unassociated information (S20). On the other hand, when both the device ID match each other (S16/Y), the storage management unit 58 stores the state information acquired in S10 in the execution information storage unit 72 by associating it with the patient ID (S18). After an endoscopic examination is ended, this patient ID is stored by being associated with execution information, thereby allowing execution information and state information to be stored by being appropriately associated with each other.

In actual medical service, a plurality of examinations are sometimes executed for one patient in one examination room 2. Before the execution of the examinations, an order for specifying the content of each examination has been issued for the examination in advance, and a doctor executes the examinations in accordance with each order. In the medical information management system 1, the number of examinations corresponds to the number of orders. For example, when an order is issued for each of an upper endoscopic examination and a lower endoscopic examination, two examinations are to be executed by using two types of the endoscope apparatuses 12. When two examinations are executed sequentially in time, or when two examinations are executed sequentially with a slight time interval, the measuring probe 32 is being attached to a fingertip of a patient, and hence the monitor device 30 periodically transmits biological information to the management apparatus 50 over the two examinations. Accordingly, the determination unit 56 may determine which of the upper endoscopic examination and the lower endoscopic examination the acquired biological information is to be associated with by using both time information on an examination in the endoscope system 10 and the acquisition time or transmission time of biological information in the monitor device 30.

Thus, the determination unit 56 may perform determination processing by using location information or by using location information and time information. When an endoscopic examination is started in the endoscope system 10, the transmission unit 20 transmits the information indicating the start time of the examination to the management apparatus 50; and when the endoscopic examination is ended, the transmission unit 20 transmits the information indicating the end time of the examination to the management apparatus 50. These start time and end time are notified to the determination unit 56, so that the determination unit 56 specifies an examination (order) with which biological information is to be associated. Alternatively, the transmission unit 20 may transmit, to the determination unit 56, the information indicating the start or end of an endoscopic examination, not the information indicating time, so that the determination unit 56 specifies the start time or the end time from the time when receiving the information.

An embodiment will be described, in which a lower endoscopic examination is executed after an upper endoscopic examination is executed. It is assumed that the determination unit 56 receives the following start time and end time for each endoscopic examination:

Start time of upper endoscopic examination: 10:00
End time of upper endoscopic examination: 10:15
Start time of lower endoscopic examination: 10:20
End time of lower endoscopic examination: 10:40.

Biological information is transmitted from the monitor device 30 to the management apparatus 50 at intervals of 1 second. The storage management unit 58 stores, at intervals of 5 minutes, the state information acquired by the biological information acquiring unit 54 by associating it with the patient identification information stored in the execution information storage unit 72. In this embodiment, it is assumed that: the biological information acquiring unit 54 first stores the state information acquired at 10:02 in the execution information storage unit 72; and subsequently stores the state information acquired at intervals of 5 minutes in the execution information storage unit 72.

The determination unit 56 determines that the biological information transmitted from the start time to the end time of the upper endoscopic examination, that is, the biological information transmitted at 10:02, 10:07, and 10:12 are transmitted during the execution of the upper endoscopic examination. The storage management unit 58 stores these biological information by connecting them to the order for the upper endoscopic examination. In addition, the determination unit 56 determines that the biological information transmitted from the start time and the end time of the lower endoscopic examination, that is, the biological information transmitted at 10:22, 10:27, 10:32 and 10:37 are transmitted during the execution of the lower endoscopic examination. The storage management unit 58 stores these biological information by connecting them to the order for the lower endoscopic examination. Thereby, biological information can be connected to an appropriate order when they are associated with patient identification information, even if a plurality of examinations are executed in the same location.

Alternatively, the determination unit 56 may perform determination processing by using location information and time information. Alternatively, the determination unit 56 may perform the determination processing by using time information, instead of location information. The determination processing according to the present embodiment is performed on the first condition that the patient ID stored in the execution information storage unit 72 matches that transmitted from the monitor device 30. When this first condition is satisfied, the determination unit 56 determines whether execution information and biological information are to be associated with each other by determining whether a further condition is satisfied. When a condition regarding a location is referred to as a second condition and that regarding time is referred to as a third condition, the determination unit 56 can accurately associate execution information and biological information with each other, when the second condition and the third condition are made to be requirements for the association processing, in addition to the satisfaction of the first condition.

Alternatively, the determination unit 56 may determine that execution information and biological information are to be associated with each other, when at least one of the second condition and the third condition is satisfied, in addition to the satisfaction of the first condition. With the satisfaction of at least one of the second condition and the third condition in addition to the first condition, it becomes possible to properly associate execution information and biological information with each other. The satisfaction of the third condition indicates that execution information and biological information are generated in the same time frame. Even when the satisfaction of each of the first condition and the third condition is made to be a requirement for the association processing, sufficiently high accuracy can be ensured.

In the medical information management system 1 according to the present embodiment, execution information and biological information are essentially associated with each other in advance. Accordingly, when creating a report for an endoscopic examination, a doctor creates it by referring to an endoscope image file included in the execution information and the biological information at the time. However, a situation can occur, as stated above, in which biological information is not associated with execution information and is stored in the storage device 70 as unassociated information.

Accordingly, when creating a report, a doctor inputs, from the input unit 66, an instruction for displaying candidates for biological information when the biological information is not associated with execution information. Upon receiving this instruction, the candidate extracting unit 60 displays, on the display 64, the patient identification information connected to the biological information stored as unassociated information by reading out them from the unassociated information storage unit 76. In this case, the candidate extracting unit 60 may display, on the display 64, the time when the biological information is first transmitted and the time when it is finally transmitted by reading out them. Alternatively, the input unit 66 and the display 64 may be a client apparatus for providing a report creating function to a doctor. A doctor specifies the biological information to be associated with execution information by watching the displayed information. For example, when the patient identification information in execution information and that in biological information match each other, a doctor may specify the biological information to be associated with the execution information based on time information. Further, even when the patient identification information in execution information and that in biological information do not match each other, but when the information on the time when the biological information is transmitted matches the time frame when an endoscopic examination has been executed, a doctor may specify the biological information to be associated with the execution information by determining that the patient identification information has been erroneously inputted to the monitor device 30. When a doctor inputs, from the input unit 66, an instruction for specifying biological information, the matching processor 62 supplies the information on the specified biological information to the storage management unit 58. Thereby, the storage management unit 58 can associate the biological information stored in the unassociated information storage unit 76 with the execution information stored in the execution information storage unit 72.

As stated above, a user interface for associating biological information with execution information may be provided to a doctor; however, a user interface for associating execution information with biological information may also be provided.

The present invention has been described above based on exemplary embodiments. The exemplary embodiments are intended to be illustrative only and various combinations of elements of the exemplary embodiments are also within the scope of the present invention. An exemplary embodiment obtained by combining the described exemplary embodiments has an advantage that is a combination of respective advantages of constituent exemplary embodiments. Various modifications, such as design modification, could be developed based on the knowledge of those skilled in the art and such modifications are also within the scope of the present invention.

In an embodiment, the corresponding information holding unit 74 holds both location information for specifying a location where medical practice is executed and device identification information on a device installed in the location, by mapping them to each other. The content of the information held by the corresponding information holding unit 74 may be manually registered by a system manager when the device is installed. However, a network device, such as the monitor device 30, is sometimes moved to be used in another examination room or replaced for maintenance. Thus, the location where a network device is arranged is sometimes changed, and hence it is desirable to appropriately set location information in the corresponding information holding unit 74 after a device is moved.

Accordingly, the present inventor has paid attention to a device that is less likely to be moved in the network 4, and has thought that location information on a network device is managed by using this device. Specifically, a router is hardly to be moved in the network 4 and is fixedly arranged. Therefore, the management apparatus 50 is designed to have a holding unit in advance, in which the router and a location where the router is installed are mapped to each other. The management apparatus 50 can map, in the corresponding information holding unit 74, the identification information on a network device to a location where the network device is installed by communicating with the network device to specify a router located in the upstream of the network device. By periodically performing this check processing, the management apparatus 50 can make the corresponding information holding unit 74 to appropriately hold the correspondence relationship between the network device and the location where the network device is installed.

In an embodiment, the monitor device 30 is arranged in the examination room 2, and the corresponding information holding unit 74 holds the location information for specifying the examination room 2 and the device identification information (MAC address) of the monitor device 30, by mapping them to each other. When the monitor device 30 is fixedly arranged in the examination room 2, as described above, the biological information acquiring unit 54 can acquire the device identification information on the monitor device 30 from the location information on the examination room 2.

When a patient undergoes an endoscopic examination, a pretreatment is executed before the endoscopic examination, so that biological information on the patient is monitored. When the endoscopic examination is ended, the patient is carried to a recovery room, where biological information after the endoscopic examination is observed for a certain period of time. In a case that the monitor devices 30 are arranged in each of the pretreatment room and the recovery room, it will be explained below a method of associating the biological information acquired by each monitor device 30 with the execution information on the endoscopic examination.

In the phase of the pretreatment, the biological information acquiring unit 54 first acquires the patient identification information and the biological information transmitted from the monitor device 30 installed in the pretreatment room. In this case, when the execution information storage unit 72 stores the location information on a room where a pretreatment of an endoscopic examination is performed, and when the corresponding information holding unit 74 holds location information for specifying a pretreatment room and device identification information on the monitor device 30, by mapping them to each other, the biological information acquired by the monitor device 30 can be associated with the record of an order for the endoscopic examination, as described with respect to the examination room 2.

On the other hand, when location information on a pretreatment room is not included in the order, and when the execution information storage unit 72 does not store location information on a pretreatment room, the storage management unit 58 stores, in the unassociated information storage unit 76, the patient identification information and the biological information acquired from the monitor device 30 as unassociated information. When a pretreatment is ended and an endoscopic examination is started in the examination room 2, the storage management unit 58 stores the biological information acquired by the monitor device 30 in the examination room 2 by associating it with the patient identification information stored in the execution information storage unit 72, as described above.

In this case, the determination unit 56 searches whether biological information on the same patient has been stored in the unassociated information storage unit 76 before the start of the endoscopic examination. Herein, the determination unit 56 searches for biological information on the same patient, for example, within a predetermined period of time from the start time of the endoscopic examination, for example, within one hour therefrom. When finding biological information on the same patient in the unassociated information storage unit 76, the determination unit 56 recognizes that the biological information has been acquired in the phase of the pretreatment, and determines that the biological information is to be associated with the patient identification information in the order for the endoscopic examination. Thereby, the storage management unit 58 stores the biological information by associating it with the patient identification information in the execution information storage unit 72 and deletes the biological information stored in the unassociated information storage unit 76. In this case, the storage management unit 58 may physically change the storage area in the storage device 70. Alternatively, the storage management unit 58 may substantially transfer the biological information stored in the unassociated information storage unit 76 to the execution information storage unit 72 by providing, to the biological information, a link with the execution information storage unit 72.

In the recovery phase following the endoscopic examination, the biological information acquired during the pretreatment and the endoscopic examination are already associated with the execution information on the endoscopic examination. In the recovery room, the monitor device 30 is fixedly arranged, and the corresponding information holding unit 74 holds device identification information (MAC address) of the monitor device 30 and location information for specifying the recovery room where the monitor device 30 is installed by mapping them to each other. Thereby, the determination unit 56 can recognize that the biological information transmitted from the monitor device 30 in the recovery room is transmitted from the recovery room. When recognizing that execution information on the same patient is already associated with biological information (i.e., biological information acquired during the pretreatment and the examination), the determination unit 56 determines that the biological information transmitted from the recovery room is also to be associated with, so that the storage management unit 58 stores it by associating it with the patient identification information. Thus, the management apparatus 50 can also associate the biological information acquired during each phase of a pretreatment and recovery with the execution information on an endoscopic examination.

In recent years, the miniaturization of the monitor device 30 has progressed, and some of the monitor devices 30 are mobile types and have a wireless communication function. By using such the mobile type monitor device 30, a patient can move, for example, among a pretreatment room, an endoscopic examination room, and a recovery room while attaching the measuring probe 32 to a fingertip and lying on a bed. The monitor device 30 periodically transmits patient identification information and biological information to the management apparatus 50, and the biological information acquiring unit 54 stores them in the unassociated information storage unit 76. The biological information acquiring unit 54 collects the biological information connected to the same patient identification information to accumulate them in the unassociated information storage unit 76.

In order to associate the biological information stored in the unassociated information storage unit 76 with execution information on an endoscopic examination, it is needed to connect, at a certain timing, location information for specifying a location of the monitor device 30 to this biological information. Accordingly, when a patient is moved from a pretreatment room into the examination room 2 in a state of being mounted on a bed, the mobile type monitor device 30 is recognized by an RFID. The recognition by an RFID fundamentally indicates that the mobile type monitor device 30 enters the examination room 2; however, in the biological information acquiring unit 54, the recognition is treated as device arrangement information indicating that the monitor device 30 exists in the examination room 2.

In this case, the determination unit 56 determines whether the patient identification information acquired by the biological information acquiring unit 54 and the patient identification information stored in the execution information storage unit 72 match each other. When both the patient identification information match each other, the determination unit 56 determines whether the device arrangement information acquired by the biological information acquiring unit 54 and the location information stored in the execution information storage unit 72 indicate the same location. Herein, when the device arrangement information indicates the examination room 2 and the location information indicates the examination room 2, the determination unit 56 determines that both the device arrangement information and the location information indicate the same location. In this case, the determination unit 56 determines that the execution information in the endoscope system 10 and the biological information in the monitor device 30 are acquired for the same patient and are acquired in the same examination room 2. Upon receiving a determination result by the determination unit 56, the storage management unit 58 stores the biological information accumulated in the unassociated information storage unit 76 by associating it with the patient identification information stored in the execution information storage unit 72, and stores the biological information acquired thereafter by the biological information acquiring unit 54 by similarly associating it with the patient identification information stored in the execution information storage unit 72. Thereby, it becomes possible to store execution information and biological information by associating them with each other.

On the other hand, when the determination unit 56 determines that the device arrangement information and the location information do not indicate the same location, the storage management unit 58 does not associate, upon receiving the determination result, the biological information stored in the unassociated information storage unit with the execution information.

Figure 4:
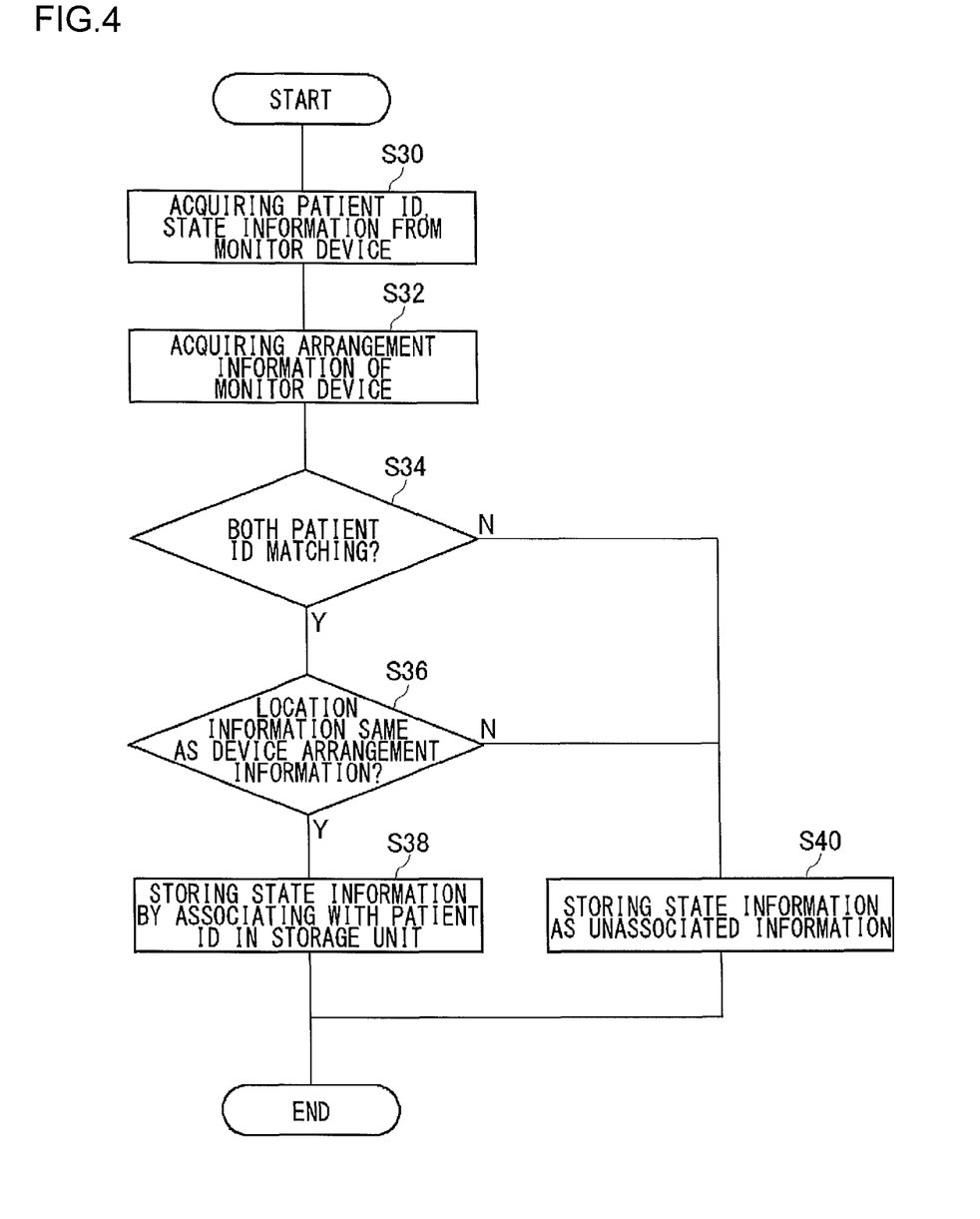
FIG. 4 is a view illustrating another example of the flowchart of the association processing by the management apparatus.

FIG. 4 illustrates another example of the flowchart of the association processing by the management apparatus 50. The biological information acquiring unit 54 acquires patient ID and state information (biological information) from the monitor device 30 (S30). In addition, the biological information acquiring unit 54 acquires the device arrangement information on the monitor device 30 from a recognition result by an RFID (S32).

The determination unit 56 determines whether the patient ID stored in S30 and that stored in the execution information storage unit 72 match each other (S34). When they do not match each other (S34/N), the storage management unit 58 stores the patient ID and the state information, which are acquired in S30, in the unassociated information storage unit 76 as unassociated information (S40). On the other hand, when they match each other (S34/Y), the determination unit 56 determines whether the device arrangement information acquired in S32 and the location information stored in the execution information storage unit 72 indicate the same location (S36). When the location information and the device arrangement information do not indicate the same location (S36/N), the storage management unit 58 stores the patient ID and state information, which are acquired in S30, in the unassociated information storage unit 76 as unassociated information (S40). On the other hand, when they indicate the same location (S36/Y), the storage management unit 58 stores the state information acquired in S30 in the execution information storage unit 72 by associating it with the patient ID (S38). Thereby, it becomes possible to store execution information and state information by appropriately associating them with each other. Alternatively, the determination unit 56 may perform the determination processing by using not only location information but also time information.

What is claimed is:

1. A medical information management system comprising:
    a management apparatus operative to manage information on medical practice for a patient; and
    a device able to communicate with the management apparatus via a network, wherein
    the device includes:
    an input unit operative to input patient identification information;
    a first acquiring unit operative to acquire state information on a state of a patient; and
    a transmission unit operative to transmit the patient identification information and the state information, and wherein
    the management apparatus includes:
    a second acquiring unit operative to acquire the patient identification information, the state information, and identification information on the device;
    a holding unit operative to hold both location information for specifying a location where medical practice is executed and identification information on a device installed in the location, by mapping them to each other;
    a storage unit operative to store execution information on medical practice for a patient by mapping it to the patient identification information and the location information for specifying a location where medical practice has been executed;
    a determination unit operative to determine, when the patient identification information acquired by the second acquiring unit matches the patient identification information stored in the storage unit, whether the device identification information acquired by the second acquiring unit is the same as the device identification information mapped to the location information stored in the storage unit; and
    a storage management unit operative to store, when it is determined that both the device identification information are the same as each other, the state information acquired by the second acquiring unit in the storage unit by associating it with the patient identification information.

2. The medical information management system according to claim 1, wherein
    when the determination unit determines that both the device identification information are not the same as each other, the storage management unit stores the patient identification information and the state information, which are acquired by the second acquiring unit, in the storage unit as unassociated information.

3. The medical information management system according to claim 1, wherein
    the determination unit determines whether the state information acquired by the second acquiring unit is to be associated with the patient identification information by using information indicating a start time of the medical practice.

4. The medical information management system according to claim 3, wherein
    the determination unit determines that the state information, acquired before a predetermined period of time from the start time of the medical practice, is to be associated with the patient identification information.

5. A management apparatus operative to store execution information of medical practice for a patient by associating it with state information on a patient acquired by medical equipment, the management apparatus comprising:
    an acquiring unit operative to acquire patient identification information and state information, which are acquired by the medical equipment, and identification information on the medical equipment;
    a holding unit operative to hold both location information for specifying a location where medical practice is executed and identification information on medical equipment installed in the location, by mapping them to each other;
    a storage unit operative to store execution information on medical practice for a patient by mapping it to patient identification information and location information for specifying a location where medical practice has been executed;
    a determination unit operative to determine, when the patient identification information acquired by the acquiring unit matches the patient identification information stored in the storage unit, whether the device identification information acquired by the acquiring unit is the same as the device identification information mapped to the location information stored in the storage unit; and
    a storage management unit operative to store, when it is determined that both the device identification information are the same as each other, the state information acquired by the acquiring unit in the storage unit by associating it with the patient identification information.

* * * * *